United States Patent [19]

Bibby et al.

[11] Patent Number: 4,903,688

[45] Date of Patent: Feb. 27, 1990

[54] TOOTH CLEANING TOOTHBRUSH AND SYSTEM

[76] Inventors: Kenneth Bibby, 222 Codman Rd., Norwood, Mass. 02062; Frank R. Ring, Jr., 477 East St., Walpole, Mass. 02081

[21] Appl. No.: 352,712

[22] Filed: May 11, 1989

Related U.S. Application Data

[63] Continuation of Ser. No. 151,451, Feb. 2, 1988, abandoned.

[51] Int. Cl.⁴ .................. A61H 9/00; A61G 17/02
[52] U.S. Cl. .................................. 128/66; 433/80; 433/88; 433/216
[58] Field of Search ............ 178/62 A, 66; 433/80, 433/88, 216

[56] References Cited

U.S. PATENT DOCUMENTS

| | | | |
|---|---|---|---|
| 105,135 | 7/1870 | Shepard | 128/66 |
| 1,573,749 | 2/1926 | Ross Jr. | 128/62 A |
| 2,303,667 | 12/1942 | Taborski | 128/62 A |
| 2,757,668 | 8/1956 | Saladin | 128/66 |
| 2,813,529 | 11/1957 | Ikse | 128/62 A |
| 3,214,775 | 11/1965 | Murov et al. | 128/62 A |
| 3,593,707 | 7/1971 | Pifer | 128/62 A |
| 3,823,710 | 7/1974 | Borden | 128/62 A |
| 3,909,867 | 10/1975 | Hogsell | 433/80 |
| 4,303,064 | 12/1981 | Buffa | 128/62 A |
| 4,319,595 | 3/1982 | Ulrich | 128/62 A |
| 4,429,434 | 2/1984 | Sung-shan | 132/84 R |
| 4,538,631 | 9/1985 | Prince | 433/91 |
| 4,620,528 | 11/1986 | Arraval | 128/66 |
| 4,743,199 | 5/1988 | Weber et al. | 433/80 |
| 4,806,277 | 2/1989 | Sakurai et al. | 252/626 |

Primary Examiner—John J. Wilson
Attorney, Agent, or Firm—Timothy A. French

[57] ABSTRACT

A system for the removal of plaque and other unwanted debris from the teeth of a user includes a toothbrush having a handle, a distal head, and a multiplicity of bristles. Each bristle includes a shaft having a base associated with a surface of the head, the shaft extending away from the surface and terminating in a proximal end disposed in relation to proximal ends of other shafts for mutual engagement with teeth surfaces of a user. The multiplicity of bristles define between themselves a multiplicity of interconnected restricted flow pathways. The surface of the head defines an orifice surrounded by the bases of the bristles. A conduit has a distal end terminating in the orifice. The bristles, in combination with the surface of the proximal end of the conduit supplies a flow of low pressure air through the conduit and the orifice into the enclosed volume, the flow of air from the orifice combining with a liquid dispersed in the pathways between the bristles so as to form a multiplicity of small bubbles within the pathways. The bubbles are directed by the orifice and driven by the air flow along the pathways and impact against the engaged teeth surfaces and burst to remove plaque and other debris from the teeth surfaces.

8 Claims, 1 Drawing Sheet

TOOTH CLEANING TOOTHBRUSH AND SYSTEM

This is a continuation of application Ser. No. 07/151,451, filed Feb. 2, 1988, now abandoned

BACKGROUND OF THE INVENTION

This invention relates to systems for cleaning the teeth in which a flow of air is delivered to the surfaces of the teeth to aid in the removal of plaque and other debris. The air may be combined with liquid to enhance the cleaning effect, for example via bubbles forming in the liquid and bursting against the teeth.

Borden, U.S. Pat. No. 3,823,710, discloses a toothbrush having an outlet orifice situated distal to the bristle cluster on the toothbrush head, for delivery of pulsed air. The orifice consists of a pair of concentric seals having sufficient resiliency to effectively seal against the tooth or guns. Scrubbing action is effected when a space between the teeth is uncovered and a major pulse or puff of air is released "[B]ubbling and release of the gases from beneath the double seals of the tip element, do a highly efficient job in dislodging and removing the plague so that a minimum amount effort and time is then required by the user" (col. 4, lines 56–60).

SUMMARY OF THE INVENTION

In one aspect the invention features a system for the removal of plaque and other unwanted debris from the teeth of a user including a toothbrush having a handle, a distal head, and a multiplicity of bristles each including a shaft having a base associated with a surface of the head, the shaft extending away from the surface and terminating in a proximal end disposed in relation to proximal ends of other shafts for mutual engagement with teeth surfaces of a user, the multplicity of bristles defining between themselves a multiplicity of interconnected restricted flow pathways, the surface of the head defining an orifice surrounded by the bases of the bristles, means defining a conduit having a distal end terminating in the orifice, the bristles, in combination with the surface of the head and the teeth surfaces, forming an enclosed volume, a source of low pressure air associated with the proximal end of the conduit for supplying a flow of low pressure air through the conduit and the orifice into the enclosed volume, the flow of air from the orifice combining with a liquid dispersed in the pathways between the bristles so as to form a multiplicity of small bubbles within the pathways, the bubbles being directed by the orifice and driven by the air flow along the pathways and impacting against the engaged teeth surfaces and bursting to cause plaque and other debris to be removed from the teeth surfaces.

In preferred embodiments of the system, the source also includes means for adding liquid to the flow of air, the air and liquid passing through the conduit to the orifice and into the enclosed volume such that the liquid is dispersed throughout the bristles. The source includes a low pressure air pump, and a tube connecting the pump to the proximal end of the conduit, and the means for adding includes a sealed chamber containing the liquid and connected to the tube.

In another aspect the invention features a toothbrush for use with the described system.

In preferred embodiments of both aspects of the invention, the multiplicity of bristles are arranged on the head surface in multiplicity of rows. The conduit is arranged to receive and carry a combination of air and liquid, and the orifice is arranged to direct the combination into the enclosed volume so as to disperse the liquid in the pathways between the bristles.

These and other features and advantages of the invention will be apparent from the following description of a preferred embodiment, and from the claims.

DESCRIPTION OF THE PREFERRED EMBODIMENT

We first briefly describe the drawings.

STRUCTURE

Figure 1:
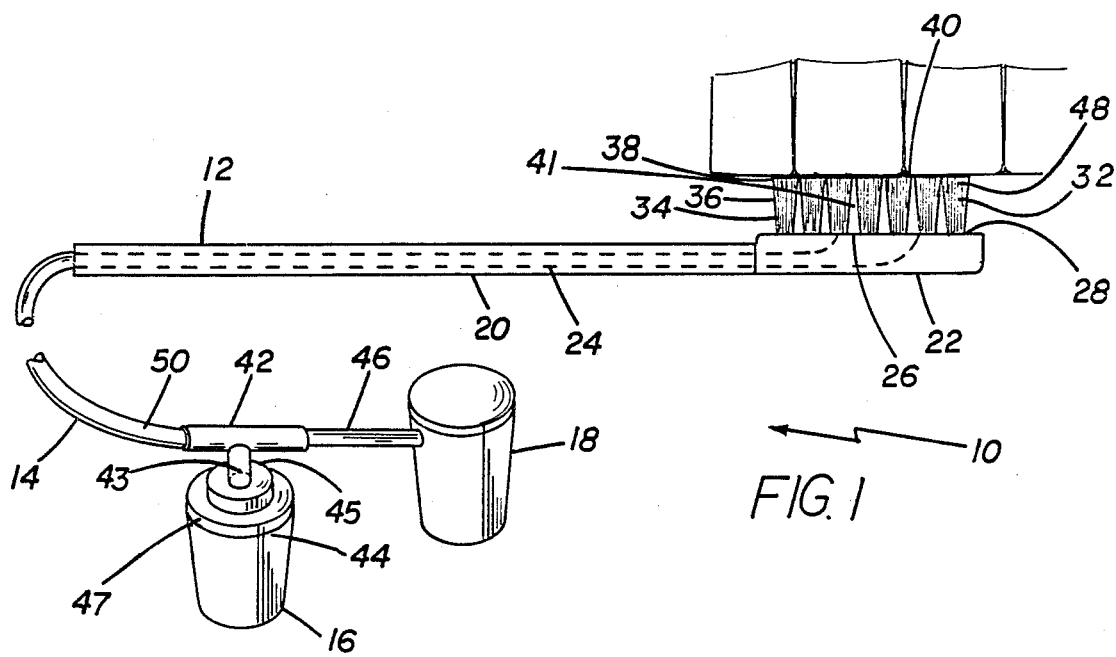
FIG. 1 is a side view of the system of the invention, including a toothbrush, connected to a low pressure source of air and liquid.
Figure 2:
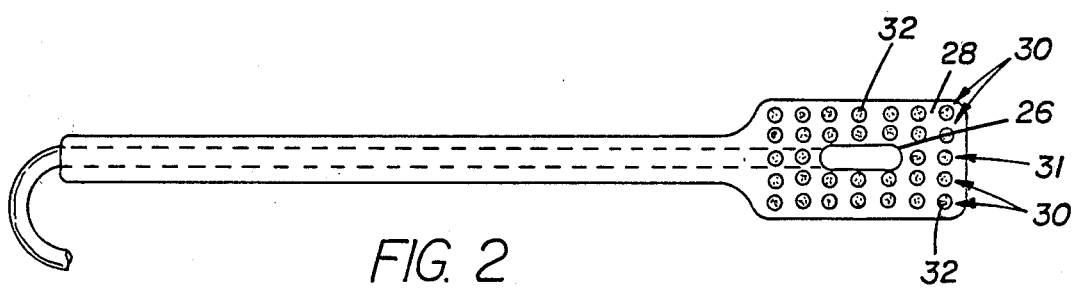
FIG. 2 is a plan view of the toothbrush of FIG. 1.

Referring to FIGS. 1 and 2, a teeth cleaning system 10 includes a toothbrush 12 connected via a tube 14 to a liquid reservoir 16 and a low pressure air pump 18. Toothbrush 12 includes a handle 20 and a head 22, which together define a conduit 24 connected at the proximal end of handle 20 to tube 14 and terminating in an orifice 26 in a surface 28 of head 22. Disposed on head surface 28 are a multiplicity of bristles 34 divided into bristle groups 32 each containing a multiplicity of bristles. Bristle groups 32 are arranged in four rows 30 each containing, e.g., seven groups 32, and one row 31 containing, e.g., four groups 32. Each bristle 34 includes a shaft 36 attached at a distal end to head surface 28 and having a proximal end 38 disposed in relation to proximal ends of other shafts so as to mutually engage a tooth surface 40. Defined between bristles 34 and extending from surface 28 to tooth surface 40 are a multiplicity of interconnected restricted flow pathways 48. Bristles 34 surround orifice 26 and, together with head surface 28 and tooth surface 40, form an enclosed volume 41.

Tube 14 is made of flexible plastic tubing and is connected to one arm of a T-fitting 42. Another arm of T-fitting 42 is connected to an opening 43 in the top 45 of liquid reservoir 16. Reservoir 16 contains a liquid (e.g. water, or a dentrifrice) 44 and an air gap 47 situated between the surface of liquid 44 and opening 43 in the top 45 of reservoir 16. The final arm of T-fitting 42 is connected, via a tube 46, to air pump 18 (e.g. a typical aquarium pump) capable of providing an air flow of 50 cfh (cubic feet per hour).

OPERATION

In operation, a user of teeth cleaning system 10 turns on pump 18 causing air to flow at low pressure, e.g., 50 cfh, through tube 46 and T-fitting 42 into air gap 47 in reservoir 16 and through tube 14, conduit 24, and orifice 26 into the enclosed volume 41. To cause liquid to be carried from reservoir 16 to the bristles of the toothbrush, the user pinches tube 14 at a point 50, resulting in a pressure buildup in air gap 47. Upon releasing the tube, a small amount of liquid will be drawn up through T-fitting 42 and carried by the air flow into enclosed volume 41. Once within enclosed volume 41, liquid 44 disperses into the pathways between bristles 34.

As the user applies the bristles of the toothbrush to teeth surfaces (e.g. 40), air flowing from the orifice into the bristles combines with the liquid dispersed in the pathways to form a multiplicity of small bubbles. The air flow drives the bubbles along pathways 48 in the direction of the tooth surface 40. The shafts of the bristles 34 flare outward from the base, and the widening of pathways 48 causes the bubbles to flow generally toward teeth surfaces 40. The bubbles driven against teeth surfaces 40 burst causing plaque and other debris to be loosened and eventually removed from the tooth surface.

MANUFACTURE

Referring again to FIG. 1, toothbrush 12 can be manufactured according to a variety of methods. In one method, a conventional toothbrush having five rows each containing seven bristle groups is modified to form toothbrush 26. The three central bristles from the center row are pulled out and a hole is drilled forming orifice 26 and one end of conduit 24. Another hole is drilled from the proximal end of handle 20 to form the remainder of conduit 24. Tube 14 may be fitted inside conduit 24 or connected to a fitting extending from the conduit.

Alternatively, toothbrush 26 can be injection molded with conduit 24 preformed.

Figure 3:
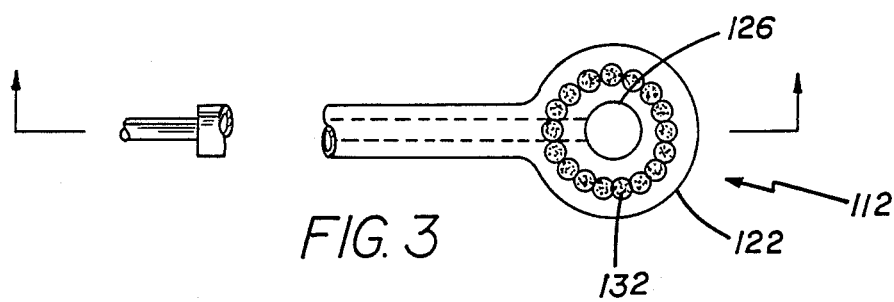
FIG. 3 is a plan view of another embodiment of a toothbrush of the present invention.
Figure 4:
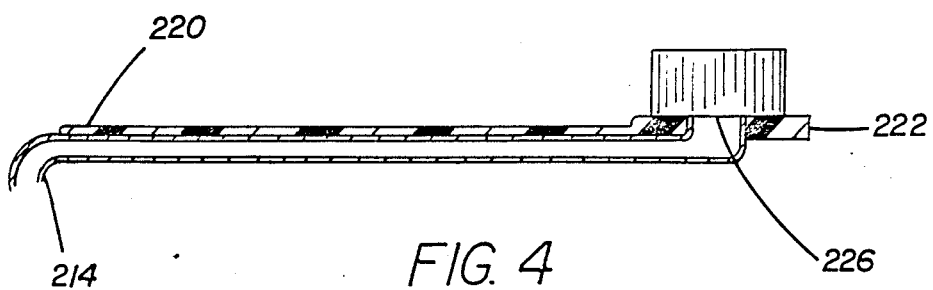
FIG. 4 is a side section view of still another embodiment of toothbrush of the present invention.

Other embodiments are within the following claims. For example, referring to FIG. 3, head 122 of toothbrush 112 can be round, and bristle groups 132 can be arranged in a circle surrounding orifice 126. Referring to FIG. 4, in another embodiment tube 214 extends along an outer surface of handle 220, terminating in orifice 226 in head 222.

What is claimed is:

1. A system for the removal of plaque and other unwanted debris from the teeth of a user comprising
   a toothbrush comprising
      a handle,
      a distal head, and
      a multiplicity of bristles each comprising a shaft having a base associated with a surface of said head, said shaft extending away from said surface and terminating in a proximal end disposed in relation to proximal ends of other said shafts for mutual engagement with teeth surfaces of a user, said multiplicity of bristles defining a multiplicity of interconnected restricted flow pathways therebetween.
   said surface of said head defining an orifice surrounded by the bases of said bristles,
   means defining a conduit having a distal end terminating in said orifice,
   said bristles, in combination with said surface of said head and said teeth surface, forming an enclosed volume,
   a source of low pressure air associated with the proximal end of said conduit for supplying a flow of low pressure air through said conduit and said orifice into said enclosed volume,
   means for dispersing liquid in said multiplicity of interconnected restricted flow passageways between said bristles to form a moist environment within said closed volume,
   means for delivering said flow of air from said orifice to combine with the liquid dispersed in said pathways between said bristles in a manner to form a multiplicity of small, air-containing bubbles within said pathways, and
   means for directing said air-containing bubbles along said pathways and means for driving said air-containing bubbles to burst with impulsive force against the engaged teeth surfaces in a manner to remove plaque and other debris from said teeth surfaces.

2. The system of claim 1, wherein said multiplicity of bristles are arranged in said head surface in a multiplicity of rows.

3. The system of claim 1, wherein said means for dispersing liquid in said pathways comprises means for adding liquid to the flow of air from said low pressure source, said air and liquid passing through said conduit to said orifice and into said enclosed volume.

4. The system of claim 3 wherein said source comprises
   a low pressure air pump, and
   a tube connecting said pump to said proximal end of said conduit, and
   said means for adding liquid comprises a sealed chamber containing the liquid and connected to said tube.

5. A toothbrush for use with a system for the removal of plaque and other unwanted debris from the teeth of a user, said system including a low pressure source of air, said toothbrush comprising
   a handle,
   a distal head,
   a multiplicity of bristles each comprising a shaft having a base associated with a surface of said head, said shaft extending away from said surface and having a proximal end disposed in relation to proximal ends of other said shafts for mutual engagement with teeth surfaces of a user, said multiplicity of bristles defining a multiplicity of interconnected restricted flow pathways therebetween,
   said multiplicity of bristles further adapted to receive a dispersion of liquid in said multiplicity of interconnected restricted flow pathways between said bristles to form a moist environment within said closed volume,
   said head surface defining an orifice surrounded by the bases of said bristles, and
   means defining a conduit having a distal end terminating in said orifice,
   said bristles, in combination with said surface of said head and said tooth surfaces, forming an enclosed volume,
   said conduit being arranged to receive a flow of air from said source at a proximal end of said conduit and to carry said air to said orifice, said orifice being arranged to direct said flow of air into the moist environment of said enclosed volume, said pathways within said enclosed volume being arranged to combine with flow of air with the liquid dispersed in said pathways between said bristles so as to form a multiplicity of small, air-containing bubbles, said pathways being further arranged to direct said air-containing bubbles along said pathway in the direction of said teeth surfaces, and means for draining said air-combining bubbles to burst with impulsive force against the engaged teeth surfaces in a manner to remove plaque and other debris from the teeth surfaces.

6. The toothbrush of claim 5 wherein said multiplicity of bristles are arranged on said surface of said head in a multiplicity of rows.

7. The toothbrush of claim 5 wherein
   said conduit is arranged to receive and carry a combination of air and liquid, and said orifice is arranged to direct said combination into said enclosed volume so as to disperse the liquid in said pathways between said bristles.

8. A system for the removal of plaque and other unwanted debris from the teeth of a user comprising
a toothbrush comprising
a handle,
a distal head, and
a multiplicity of bristles each comprising a shaft having a base associated with a surface of said head, said shaft extending away from said surface and having a proximal end disposed in relation to proximal ends of other said shafts for mutual engagement with teeth surfaces of a user, said multiplicity of bristles defining a multiplicity of interconnected restricted flow pathways therebetween,
said surface of said head defining an orifice surrounded by the bases of said bristles,
means defining a conduit having a distal end terminating in said orifice,
said bristles, in combination with said surface of said head and said tooth surfaces, forming an enclosed volume containing said orifice and said multiplicity of bristles,
a source of low pressure air associated with the proximal end of said conduit for supplying a flow of low pressure air through said conduit and said orifice into said enclosed volume, said source comprising
a low pressure source of air, and
a tube connecting said source to said proximal end of said conduit, and
a sealed chamber containing said liquid and connected to said tube,
means for dispersing liquid in said multiplicity of interconnected restricted flow passageways between said bristles to form a moist environment within said closed volume,
means for delivering said flow of air from said orifice to combine with the liquid dispersed in said pathways between said bristles in a manner to form a multiplicity of small, air-containing bubbles within said pathways, and
means for directing said air-containing bubbles along said pathways, and means for driving said air-containing bubbles to burst with impulsive force against the engaged teeth surfaces in a manner to remove plaque and other debris from said teeth surfaces.

* * * * *

UNITED STATES PATENT AND TRADEMARK OFFICE
CERTIFICATE OF CORRECTION

PATENT NO. : 4,903,688

DATED : 02/27/90

INVENTOR(S) : Kenneth Bibby

It is certified that error appears in the above-identified patent and that said Letters Patent is hereby corrected as shown below:

In the abstract, insert --head and the teeth surfaces, forms an enclosed volume. A source of low pressure air associated with the-- before "proximal" (line 14).

Col. 1, line 19, "gums" should be --gums--.

Col. 1, line 68, insert --a-- after "in".

Col. 3, line 45, insert "," after "therebetween".

Col. 3, line 51, "surface" should be "surfaces".

Col. 4, line 57, "way" should be --ways--.

Col. 4, line 58, "draining" should be --driving--.

Signed and Sealed this

Twenty-ninth Day of October, 1991

Attest:

HARRY F. MANBECK, JR.

*Attesting Officer*  *Commissioner of Patents and Trademarks*